(12) United States Patent
Betts

(10) Patent No.: US 7,572,249 B2
(45) Date of Patent: Aug. 11, 2009

(54) MERCHANDISE DISPLAY SYSTEMS FOR BABY CARE ARTICLES

(75) Inventor: Tysonn Yuievonn Betts, Colerain Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/607,240

(22) Filed: Dec. 1, 2006

(65) Prior Publication Data

US 2008/0128308 A1 Jun. 5, 2008

(51) Int. Cl.
*A61F 13/15* (2006.01)
*A61B 19/02* (2006.01)
*B65D 85/00* (2006.01)

(52) U.S. Cl. .............................. 604/385.01; 604/385.02; 206/438; 206/440; 206/459.5

(58) Field of Classification Search ............ 604/385.01, 604/385.02; 206/278, 524.1, 440, 438, 459.5
See application file for complete search history.

(56) References Cited

U.S. PATENT DOCUMENTS

| | | |
|---|---|---|
| 414,637 A | 11/1889 | Goodson |
| 416,794 A | 12/1889 | Mathieu |
| 421,901 A | 2/1890 | Breher |
| 421,902 A | 2/1890 | Britz |
| 437,686 A | 10/1890 | Geddes |
| 443,451 A | 12/1890 | Hunter |
| 443,508 A | 12/1890 | Emmet |
| 445,329 A | 1/1891 | Kerr |
| 451,279 A | 4/1891 | Sailor |
| 3,967,756 A | 7/1976 | Barish |
| 3,982,659 A | 9/1976 | Ross |
| 3,994,417 A | 11/1976 | Boedecker |
| 4,471,881 A | 9/1984 | Foster |
| 4,840,270 A | 6/1989 | Caputo et al. |
| 4,966,286 A | 10/1990 | Muckenfuhs |
| 4,971,220 A | 11/1990 | Kaufman et al. |
| 5,050,737 A | 9/1991 | Joslyn et al. |
| 5,065,868 A | 11/1991 | Cornelissen et al. |
| 5,242,057 A | 9/1993 | Cook et al. |
| 5,284,263 A | 2/1994 | Papciak |
| 5,322,178 A | 6/1994 | Foos |

(Continued)

FOREIGN PATENT DOCUMENTS

WO WO-99/55213 A1 11/1999

(Continued)

OTHER PUBLICATIONS

U.S. Appl. No. 11/712,181, filed Feb. 28, 2007, Tysonn Yuievonn Betts, et al.

(Continued)

*Primary Examiner*—Jacqueline F. Stephens
(74) *Attorney, Agent, or Firm*—John P. Colbert

(57) ABSTRACT

A merchandise system for disposable absorbent articles is provided. The merchandise display system includes a first line-up and second line-up of disposable absorbent articles designed to match a wearer's stage of development. The system also includes various color schemes associated with the first and second line-ups in order to facilitate consumers' identification and selection of the appropriate absorbent article configuration for a particular wearer. A merchandise system for baby care articles is also provided.

18 Claims, 3 Drawing Sheets

U.S. PATENT DOCUMENTS

| | | | |
|---|---|---|---|
| 5,366,104 | A | 11/1994 | Armstrong |
| 5,377,853 | A | 1/1995 | Papciak |
| 5,443,161 | A | 8/1995 | Jonese |
| 5,485,919 | A | 1/1996 | Samberg et al. |
| 5,591,155 | A | 1/1997 | Nishikawa et al. |
| 5,599,620 | A | 2/1997 | Huskey |
| 5,647,506 | A | 7/1997 | Julius |
| 5,785,179 | A | 7/1998 | Buczwinski et al. |
| 5,791,465 | A | 8/1998 | Niki et al. |
| 5,839,585 | A | 11/1998 | Miller |
| 5,885,264 | A | 3/1999 | Matsushita |
| 5,944,237 | A | 8/1999 | Gouldson |
| 6,024,094 | A | 2/2000 | Utecht |
| 6,092,690 | A | 7/2000 | Bitowft et al. |
| 6,168,022 | B1 | 1/2001 | Ward et al. |
| 6,229,061 | B1 | 5/2001 | Dragoo et al. |
| 6,269,969 | B1 | 8/2001 | Huang et al. |
| 6,269,970 | B1 | 8/2001 | Huang et al. |
| 6,296,144 | B1 | 10/2001 | Tanaka et al. |
| 6,315,114 | B1 | 11/2001 | Keck et al. |
| 6,401,968 | B1 | 6/2002 | Huang et al. |
| 6,412,634 | B1 | 7/2002 | Telesca et al. |
| 6,454,095 | B1 | 9/2002 | Brisebois et al. |
| 6,491,165 | B2 | 12/2002 | Kuske et al. |
| 6,568,530 | B2 | 5/2003 | Takahashi et al. |
| 6,601,705 | B2 | 8/2003 | Molina et al. |
| 6,648,864 | B2 | 11/2003 | Ronn et al. |
| 6,763,944 | B2 * | 7/2004 | Ronn et al. .................. 206/440 |
| 6,911,022 | B2 * | 6/2005 | Steger et al. ........... 604/385.05 |
| 2002/0064323 | A1 | 5/2002 | Chin |
| 2002/0148742 | A1 | 10/2002 | Bisbal et al. |
| 2003/0136704 | A1 | 7/2003 | Burgess |
| 2004/0010240 | A1 | 1/2004 | Ronn et al. |

FOREIGN PATENT DOCUMENTS

| | | |
|---|---|---|
| WO | WO-00/27268 A1 | 5/2000 |
| WO | WO-02/14172 A1 | 2/2002 |

OTHER PUBLICATIONS

U.S. Appl. No. 11/509,362, filed Aug. 24, 2006, Tysonn Yuievonn Betts, et al.
Advertisements: "Introducing Pampers Phases", Sep. 1991.
"Introducing New! Luvs Phases", Jan. 1992.
"Introducing! The First Specially Designed Diaper Made Just For Your Walker", Sep. 1991.
"Dial-A-Wheel", Sep. 1991.

* cited by examiner

MERCHANDISE DISPLAY SYSTEMS FOR BABY CARE ARTICLES

FIELD OF THE INVENTION

The present disclosure relates generally to merchandise display systems for baby care articles. The present disclosure also relates to merchandise display systems for facilitating consumers' identification and selection of appropriate baby care articles for children in particular stages of development.

BACKGROUND OF THE INVENTION

Disposable absorbent articles such as diapers, training pants, adult incontinence products and feminine care products are designed to absorb and contain bodily waste to prevent soiling of the body and clothing. The disposable absorbent articles typically comprise a single design available in different sizes to fit a variety of wearers ranging from newborns to active toddlers. The design of the diaper typically affects performance, such as ability to absorb and contain bodily waste. The size of the diaper typically affects fit, for example, the size of the diaper waist opening, the size of the openings around the thighs, and the length or "pitch" of the diaper.

The problem with a one design fits all approach is that a single configuration may not be appropriate for every level of activity and capability. For instance, caregivers for newborns and immobile infants may desire a soft, yet bulky design which wraps the wearer and is gently on the wearer's skin whereas once the infant becomes actively mobile it may be more desirable to have a contoured trim fit design providing the wearer more freedom of movement. Other designs may also be desired as the toddler grows and becomes more and more capable of independent activity. For instance, a pull on diaper design may be beneficial for toddlers participating in the dressing experience. Similarly, a training diaper design may be appealing to a toddler in the toilet training stage which makes a wearer aware when a discharge of bodily waste has occurred while at the same time providing the necessary protection to the wearer's clothing. It is difficult to design a single product configuration exhibiting each of these attributes. Thus, there is a need for a variety of disposable diaper designs matching a particular wearer's capability and/or level of activity.

Although providing a variety of diaper designs matching an infant or toddler's capability and/or level of activity may meet a consumer need, physical sizes of infants and toddlers vary throughout their development. As a result, different product designs are preferably made available in the same sizes. For instance, a disposable diaper designed for a crawling toddler may be available in the same size as a configuration designed for a walking toddler and/or a configuration designed for a toddler participating in the dressing experience. Merchandising systems typically display and arrange disposable diapers according to size numbers.

This proliferation of disposable diaper offerings does have its drawbacks, however. In particular, store displays may include an abundance of disposable diaper products. For example, many manufacturers offer several versions of disposable diaper products in different "tiers" or "levels". These could represent different sub-needs or different levels of technology with different corresponding price points. As a result, it can be confusing for consumers to select the proper product in terms of appropriate size/stage/features and an appropriate tier level and to navigate among the offerings for a desired product even if such basic information such as desired brand and size is known. In addition, consumers shopping for disposable diaper products often have infants or toddlers with them, resulting in less ability to intently focus upon the multiplicity of product offerings. As such, a consumer, given the overwhelming range of options, may select the wrong product (i.e., a product other than that intended) or a product which may not be optimum (i.e., wrong stage, wrong features, wrong size). Either could lead to a less than ideal use experience.

The problems discussed above with respect to the proliferation of disposable diaper offerings similarly apply to other baby care articles, for example, disposable wipes products. The field of disposable consumer products includes a wide variety of products often referred to generically as "wipes" or "wet-wipes." Typically, these products in their simplest form consist of a substrate, such a web of nonwoven material (often pre-cut into discrete sheets), which has been impregnated with an aqueous lotion (such a cleansing solution or emulsion or paste). Wipes or wet-wipes products are currently sold commercially for a wide variety of consumer applications. These include, cosmetic removal (cosmetic or make-up wipes), feminine hygiene, general face and hand cleaning, household cleaning (such as bleach impregnated wipes), automobile cleaning, and wiping of infants and toddlers such as during a diaper change. In this last category, there are a wide variety of wipes products specifically designed to be used on or for infants and toddlers which are often referred to as "baby-wipes."

While many of the wipes products referenced above are similar in their general design (for example a disposable substrate impregnated with an aqueous lotion) important differences exist. For example, it will be readily appreciated that a wipe designed for household cleaning and containing harsh ingredients is not suitable for use on skin such as for cleansing of one's face, hands, or buttocks. Even within a single sub-group of wipes—such as baby-wipes—products from even a single manufacturer may vary considerably to meet differing needs and desires of consumers. For example, baby wipes are currently offered with several variations of scent or perfumes or several lotion variations (such as versions for sensitive skin and non-sensitive versions). Other variations seen in baby wipes include different embossing patterns which may be included on the wipe substrate itself.

As with disposable diapers, the sheer number of wipes offerings generally, and baby wipes offerings in particular, make it difficult for consumers to locate and purchase a desired product readily. This may be especially true in the case of baby wipes products where consumers often shop with infants or toddlers, resulting in less ability to intently focus upon various product offerings. Additionally, as wipes products and baby wipes products in particular are adapted to a wider variety of users, it may become increasingly difficult for consumers to self-select the product or products which most appropriately meet their needs. These needs could vary on the basis of such factors as desired benefit, use situation, and the stage of development of the child who will be using the product.

Thus, there remains a need for a merchandising system for baby care articles, particularly disposable absorbent articles and disposable wipes products, that make it easier for a caregiver to select a design from a variety of configurations that matches a particular wearer's or user's needs.

SUMMARY OF THE INVENTION

In one embodiment, a merchandise display system for disposable absorbent articles is provided. The merchandise display system comprises a first line-up of disposable absorbent articles and a second line-up of disposable absorbent articles. The first line-up includes an absorbent article of a first configuration corresponding to a wearer's first stage of development, the absorbent article of the first configuration being enclosed in a first package, wherein the first package includes a first line-up color corresponding to the first line-up and a first stage color corresponding to the first stage of development; and an absorbent article of a second configuration corresponding to a wearer's second stage of development, the absorbent article of the second configuration being enclosed in a second package, wherein the second package includes the first line-up color and a second stage color corresponding to the second stage of development. The second line-up includes an absorbent article of a first configuration corresponding to a wearer's first stage of development, the absorbent article of the first configuration being enclosed in a first package, wherein the first package includes a second line-up color corresponding to the second line-up and a first stage color corresponding to the first stage of development; and an absorbent article of a second configuration corresponding to a wearer's second stage of development, the absorbent article of the second configuration being enclosed in a second package, wherein the second package includes the second line-up color and a second stage color corresponding to the second stage of development. The first line-up color and the second line-up color are different, while the first stage color associated with the first line-up and the first stage color associated with the second line-up are substantially the same and the second stage color associated with the first line-up and the second stage color associated with the second line-up are substantially the same. The first line-up and the second line-up each contain indicia which communicates a common source or brand indicator to a consumer.

In another embodiment, a merchandise display system for baby care articles is provided. The merchandise display system comprises a line-up of disposable absorbent articles and a line-up of disposable wipes products. The line-up of disposable absorbent articles includes an absorbent article of a first configuration corresponding to a wearer's first stage of development, the absorbent article of the first configuration being enclosed in a first package, wherein the first package includes a first line-up color corresponding to the line-up of absorbent articles and a first stage color corresponding to the first stage of development; and an absorbent article of a second configuration corresponding to a wearer's second stage of development, the absorbent article of the second configuration being enclosed in a second package, wherein the second package includes the first line-up color and a second stage color corresponding to the second stage of development. The line-up of disposable wipes products includes a first wipe product of a first configuration tailored to a user's first stage of development, the wipe product of the first configuration being enclosed in a first package, wherein the first package includes a second line-up color corresponding to the line-up of wipes products and a first stage color corresponding to the first stage of development; and a second wipe product of a second configuration tailored to a user's second stage of development, the wipe product of the second configuration being enclosed in a second package, wherein the second package includes the second line-up color and a second stage color corresponding to the second stage of development. The first line-up color and the second line-up color are different, while the first stage color associated with the first line-up and the first stage color associated with the second line-up are substantially the same and the second stage color associated with the first line-up and the second stage color associated with the second line-up are substantially the same. The first line-up and the second line-up each contain indicia which communicates a common source or brand indicator to a consumer.

The foregoing merchandising systems can be employed relative to baby care articles having a range of sizes and/or a variety of designs or configurations.

BRIEF DESCRIPTION OF THE DRAWINGS

While the specification concludes with claims which particularly point out and distinctly claim the invention, it is believed the various embodiments will be better understood from the following description taken in conjunction with the accompanying drawings, in which:

DETAILED DESCRIPTION OF THE INVENTION

As used herein, the term "absorbent article" refers to devices which are designed to absorb and contain bodily exudates, and, more specifically, refers to devices which are placed within, against, or in proximity to, the body of the wearer to absorb and contain the various exudates discharged from the body.

As used herein, the term "baby care article" refers to devices or products designed for babies or small children. Exemplary types of baby care articles include, but are not limited to, diapers and wipes.

As used herein, the term "caregiver" refers to a person other than the child, such as, a parent, babysitter, family member, teacher, day care worker, or other person who is able to provide sufficient assistance or supervision to a child using an absorbent article.

As used herein, the term "chassis" refers to the main structure of a diaper, with other features added to form the composite diaper structure.

As used herein, the term "diaper" refers to an absorbent article generally used by infants and incontinent persons that is worn about the lower torso of the wearer.

As used herein, the term "disposable" describes absorbent articles which are generally not intended to be laundered or otherwise restored or reused as an absorbent article (in other words, they are generally intended to be discarded after a single use, and, preferably, to be disposed of in an environmentally compatible manner).

As used herein, the term "indicia" refers to an identifying marking, which may include words and/or graphics describing a product in use.

As used herein, the term "line-up" refers to two or more products which are each sold individually, but which are each part of a broader collective offering. The individual offerings in the line-up are associated with each other by some commonality or connection. Examples of such a commonality or connection may include, but are not limited to: a common brand name, a common logo, a common color scheme, a common graphic, or any other indicia which signal that the products are related and are offerings to sub-groups within the overall group to which the line-up as a whole is offered.

References to identifying a "size" is used herein to include a direct or indirect identification of a disposable diaper or other absorbent article size, such as by number or letter (for example, "Size 3" or "Size A"), by direct description (for example, "Small" or "Large"), or by any combination thereof, and whether expressed or discernible visually, audibly or otherwise.

As used herein, the term "stage(s) of development" refers to a level of emotional and cognitive maturity and/or the physical abilities of an individual including locomotion, mobility, motor skills and coordination.

Figure 1:
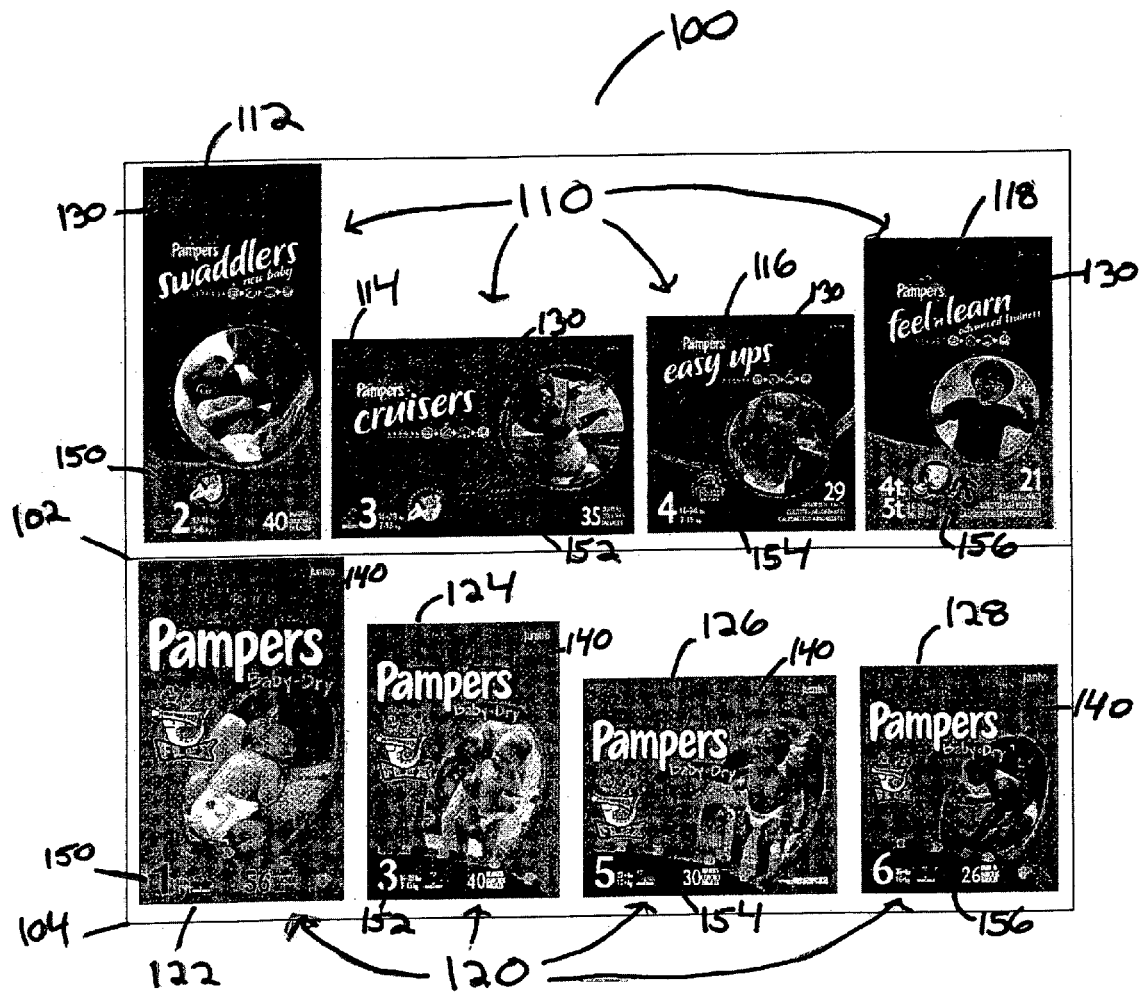
FIG. 1 illustrates an exemplary retail display of disposable absorbent articles designed to match a wearer's stage of development comprising an arrangement where each shelf carries a different line-up of disposable absorbent articles.

In one embodiment, the present disclosure is directed to a merchandise display system for disposable absorbent articles for facilitating consumers' identification and selection of the appropriate absorbent article for children in particular stages of development. For example, the disposable absorbent articles may be displayed on a shelf at a point of sale, such as within a retail store, in such a way that the different disposable absorbent article products within a line-up are visible to a consumer during the consumer's purchasing decision process. As illustrated in FIG. 1, a retail display 100 may be provided to quickly direct a consumer to disposable absorbent articles appropriate for his or her child. Retail display 100 may include a first shelf 102 and a second shelf 104, suitable for carrying disposable absorbent articles. The first shelf 102 carries a first line-up 110 of disposable absorbent articles made available in a variety of product configurations where each configuration includes distinguishable characteristics comprising structural differences addressing a wearer's stage of development. Similarly, the second shelf 104 carries a second line-up 120 of disposable absorbent articles made available in a variety of product configurations where each configuration includes distinguishable characteristics comprising structural differences addressing a wearer's stage of development. Further, the first line-up and the second line-up each contain indicia which communicates a common source or brand indicator to a consumer. As used herein, the term "brand" refers to any term, symbol, design or combination thereof that identifies and differentiates a seller's product or service which typically arise in the minds of consumers. In one example, the brand indicator includes the term PAMPERS. This example of a brand indicator is a trademark of absorbent article products manufactured by a common source, i.e. The Procter and Gamble Company. For each line-up, the stages of development may range from newborns to active toddlers seeking independence.

For example, a first stage of development might cover a pre-locomotive phase and include newborns in a bonding stage with mom and other immobile infants whose level of activity might include a little more than head raising or rolling over. A second stage of development might cover an exploring stage comprising a crawling phase and include curious toddlers developing activity in the form of sitting up and holding objects and mobility in the form of scooting, rolling, crawling and assisted walking. A third stage of development might cover a learning stage and include toddlers capable of doing things by themselves such as dressing and developing coordination which enables them to stand, walk and run without losing balance. A fourth stage of development might cover a training or teaching stage and include toddlers undergoing toilet training, attempting to achieve independence, such as climbing, and overall undergoing a transition from baby to child. Other stages are contemplated.

For each or any of the aforementioned stages of development, a separate absorbent article configuration may be provided. For example, for the first stage of development, the absorbent article configuration may comprise a chassis designed to swaddle the wearer like a blanket and include a blanket like feel. This configuration might also include special structural features like an umbilical cord notch and also ornamental features such as graphics which include pastel colors and back to sleep logos. For the second stage of development, a second absorbent article configuration may comprise a chassis designed to gently conform to the wearer in order to enable more freedom of movement. For this second configuration, the chassis might be contoured having a relatively narrow crotch region, a stretchable high back region and a low cut front region and also include bright color graphics. This configuration may also include features like flexible fasteners and high stretch sides to facilitate easy, struggle-free changes of a toddler in a standing or lying position. For the third stage of development, the third absorbent article configuration may comprise a pull on chassis designed to look more like underwear that a wearer can put on and take off enabling him or her to participate in the dressing experience. For the fourth stage of development, the fourth absorbent article configuration may comprise a chassis providing the comfort of underpants and the protection of a diaper while at the same time include a wetness indicator that enables the wearer to recognize the discomfort associated with wetting.

Since infants and toddlers experience stages of development at different rates, multiple sizes may be provided for each absorbent article configuration. As a result, different absorbent article configurations are made available in overlapping size ranges. For example, the first absorbent article configuration might be available in a size one, a size two and a size three, while the second absorbent article configuration might be available in a size three, a size four and a size five. The third absorbent article configuration might be available in a size three, a size four and a size five while the fourth absorbent article might be available in a size four, a size five and a size six, and so on.

Overlapping size ranges make it difficult for a consumer to choose the right product configuration matching a particular wearer's stage of development. For this reason, an article is provided that facilitates consumers' selection of an absorbent article from a variety of configurations.

Referring to FIG. 1, the first line-up 110 includes disposable absorbent articles 112, 114, 116 and 118 suitable for first, second, third and fourth stages of development, respectively. The second line-up 120 includes disposable absorbent articles 122, 124, 126 and 128 suitable for a first, second, third and fourth stages of development, respectively. The disposable absorbent article products within the first line-up 110 may differ in at least one product feature or product benefit from the corresponding disposable absorbent article products within the second line-up 120. For example, disposable absorbent articles 112 may have an absorb away liner while disposable absorbent articles 122 lack such a feature; disposable absorbent articles 114 may have 3-way fit while disposable absorbent articles 124 lack such a feature. Additionally, the disposable absorbent article products within the first line-up 110 may differ in retail price to the consumer from the corresponding disposable absorbent article products within the second line-up 120.

Still referring to FIG. 1, the first line-up 110 of disposable absorbent articles 112, 114, 116 and 118 and the second line-up 120 of disposable absorbent articles 122, 124, 126 and 128 can be packaged in a variety of containers such as bags, boxes or cartons. In one embodiment, as shown in FIG. 1, absorbent articles are packaged in a poly bag. In another embodiment, the packages may be a plastic "shrink-wrap" container.

In one embodiment, the first line-up 110 includes a common color scheme that is associated with the first line-up 110 of disposable absorbent articles and second line-up 120 includes a common color scheme that is associated with the second line-up 120 of disposable absorbent articles. In other words, the first line-up color and the second line-up color are different. In one example, the packages containing disposable absorbent articles 112, 114, 116 and 118 have a first line-up color 130, for example, purple, and the packages containing disposable absorbent articles 122, 124, 126 and 128 have a second line-up color 140, for example, teal. The term "color," as used herein, relates to the phenomenon of visual perception that enables one to differentiate otherwise identical objects. The use of a common color scheme across the first line-up 110 facilitates consumers' understanding that disposable absorbent articles 112, 114, 116 and 118 are each part of a broader collective offering that originate from the same company. Likewise, the use of a common color scheme across the second line-up 120 facilitates consumers' understanding that disposable absorbent articles 122, 124, 126 and 128 are each part of a broader collective offering from the same company.

The packaging for first line-up 110 and second line-up 120 also includes a stage color scheme that is associated with particular stages of development. For example, absorbent articles suitable for a first stage of development have a first stage color 150, for example, yellow, absorbent articles suitable for a second stage of development have a second stage color 152, for example, purple, absorbent articles suitable for a third stage of development have a third stage color 154, for example, red, and absorbent articles suitable for a fourth stage of development have a fourth stage color 156, for example, blue or pink. As a result, the first stage color associated with the first line-up and the first stage color associated with the second line-up are substantially the same, while the second, third and fourth stage colors associated with the first line-up are substantially the same as the second, third and fourth stage colors associated with the second line-up. The use of a stage color scheme within each line-up that is associated with a particular stage of development is used to facilitate consumers' identification and selection of the appropriate absorbent article configuration for a particular wearer.

In addition to providing a stage color scheme, the variety of absorbent article configurations may be displayed on store shelves in an arrangement that facilitates the consumer's selection. For example, the first, second, third and fourth absorbent article configurations of the first line-up, 112, 114, 116 and 118, respectively, may be arranged in a sequential order from the wearer's first stage of development to the wearer's fourth stage of development progressing from left to right across the first shelf 102. Similarly, the first, second, third and fourth absorbent article configurations of the second line-up, 122, 124, 126 and 128, respectively, may be arranged in a sequential order from the wearer's first stage of development to the wearer's fourth stage of development progressing from left to right across the second shelf 104. As a result, the system as illustrated in FIG. 1 assists consumers in selecting the appropriate product in terms of size, stage, features and line-up or tier level in order to optimize the use experience for their child.

Figure 2:
FIG. 2 illustrates an exemplary front panel of a first line-up package of disposable absorbent articles in accordance with one embodiment.

For ease of illustration and explanation an exemplary package for use with first line-up 110 will be described with reference to disposable absorbent article package 116 in particular. Referring to FIG. 2, disposable absorbent article package 116 includes a front panel 200 having a top and bottom portion and has one or more disposable absorbent articles (not shown) enclosed therein, and a stage communication system 210. In one embodiment, the stage communication system 210 includes a brand indicator 220, a line-up indicator 230 and a stage specific indicator 240, each of these indicators disposed on the front panel 200. In another embodiment, the stage communication system 210 is disposed on the top portion of the front panel 200. The stage communication system 210 communicates both brand benefits and the progressive nature of a line-up of absorbent article configurations more clearly to consumers. A more detailed description of a stage communication system disposed on a package may be found in U.S. patent application Ser. No. 11/509,362, filed Aug. 24, 2006.

Disposable absorbent article package 116 may also include an informational corridor 250 disposed on the package 116. In one embodiment, as shown in FIG. 2, the informational corridor 250 includes a size indicator, a weight range indicator, and at least one product benefit indicator, each these indicators disposed on the front panel 200. In another embodiment, the informational corridor 250 is disposed on the bottom portion of front panel 200. In yet another embodiment, two or more product benefit indicators may be provided. A more detailed description of an informational corridor disposed on a package may be found in U.S. patent application Ser. No. 11/509,362, filed Aug. 24, 2006.

Figure 3:
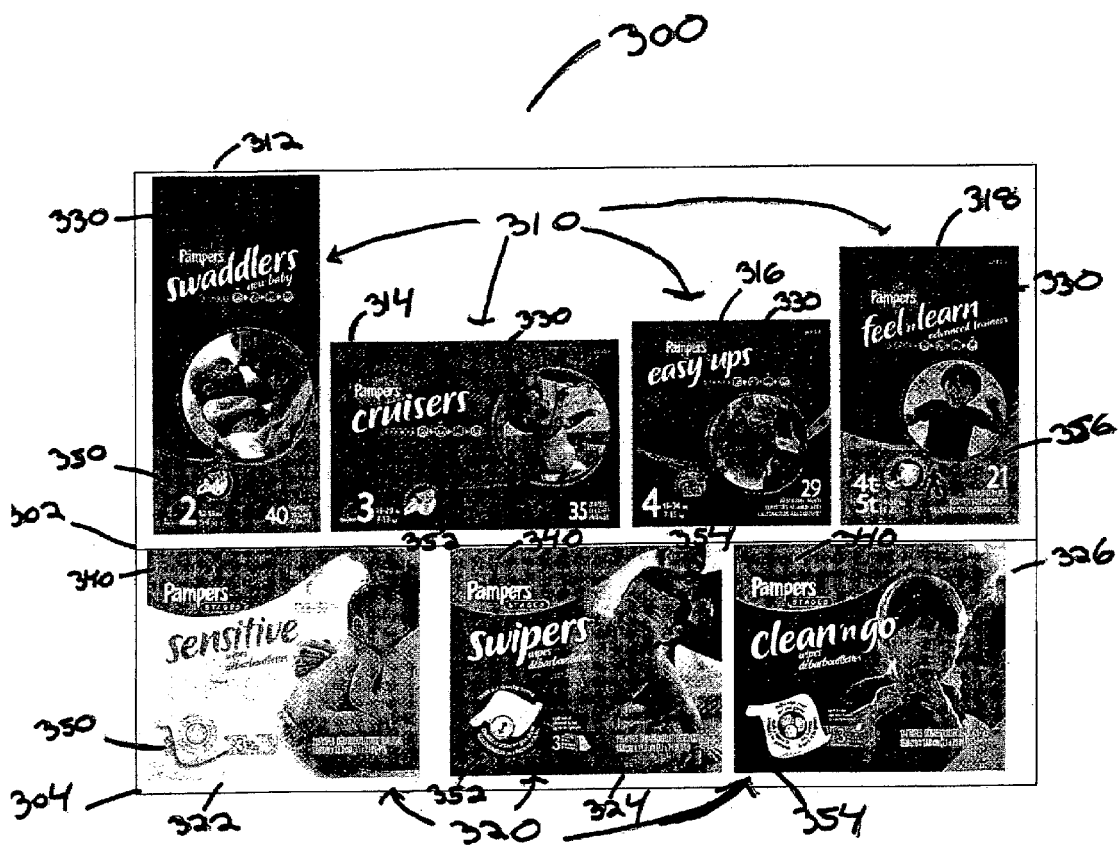
FIG. 3 illustrates an exemplary retail display of baby care articles organized by the stage of development for which the products are appropriate comprising an arrangement where the top shelf carries a line-up of disposable absorbent articles and the bottom shelf carries a line-up of disposable wipes products.

In another embodiment, the present disclosure is directed to a merchandise display system for baby care articles that are marketed by the same company. As illustrated in FIG. 3, a retail display 300 may be provided to quickly direct a consumer to baby care articles appropriate for his or her child. Retail display 300 may include a first shelf 302 and a second shelf 304, suitable for carrying baby care articles. The first shelf 302 carries a first line-up 310 of disposable absorbent articles made available in a variety of product configurations where each configuration includes distinguishable characteristics comprising structural differences addressing a wearer's stage of development. The second shelf 304 carries a second line-up 320 of disposable wipes products made available in a variety of product designs where each design includes distinguishable characteristics tailored on the basis of a user's stage of development. Further, the first line-up and the second line-up each contain indicia which communicates a common source or brand indicator to a consumer. In one example, the brand indicator includes the term PAMPERS. This example of a brand indicator is a trademark of baby care articles, for example, absorbent article products and wipes products, manufactured by a common source, i.e. The Procter and Gamble Company.

Users of baby wet wipes may comprise sub-groups each of which may have somewhat differing needs, desired benefits, or use situations. Examples of the differing needs, desired benefits, or use situations for which individual products within the line-up may be designed may include differing baby stages of development (for example, a baby in a bonding stage or a baby in a learning stage). Other examples might include use in the nursery near nap-times, and use in active situations such as with meals or at playtime. Each of the examples given above may involve different needs from, or expectations of, baby wet wipes which differ from those in other examples.

A wipes product may comprise at least a substrate. No particular design for such a wipe substrate is required and those of skill in the art will readily appreciate that all manner and variety of wipe substrates are suitable. Nonwoven materials are typical, though not required, for substrates. They may be formed into sheet-like material by any of a variety of well known processes including: airlaying, carding, spunbonding, spunlacing, hydroforming, and the like. The properties of a wipe substrate according to the present invention may be homogeneous or non-homogeneous. For example, while a single uniform web is suitable, it may be desired to have a layered substrate where fiber composition is different among some or all of the various layers. Additionally, zones of varying properties are also possible. Wipe substrate may be made from a variety of conventional natural and/or synthetic fibers including cellulosic based fibers (such as rayon, cotton, pulp, lyocell, and variations of these), or polyethylene, polypropylene, bicomponent or other synthetic fibers.

Wipes suitable for use in line-ups as described herein may be provided in a wide variety of convenient shapes and sizes although there is no particular shape or size which is necessary. For ease of manufacture and dispensing, rectangular sheets of wipe material may be used, although wipes can also be rounded, circular, or other shapes. Individual sheets can be separately packaged (such as in an interleaved "pop up" configuration) or the wipes can be packaged in a continuous stack or roll to be separated later by the user (e.g., by perforations or the like).

For ease of illustration and explanation wipes products of the present disclosure will be described with reference to wet wipes and baby wet wipes in particular. As used in this application the term "wet wipes" means a wipe product which has a moisture content of greater than about 10% by weight of the substrate. Some wipes products are delivered in an apparent "dry" state although they have measurable moisture content. For example, some cleansing wipes (such as for bathing, face washing, or makeup removal) have a low moisture content (typically less than about 10%) cleansing solution which is impregnated or otherwise integrated with the wipe substrate. This solution may be released from the wipe upon immersing the wipe in water. Wet wipes often have higher moisture content as packaged, such as moisture content in the range from about 50% to about 350% or more by weight. For purposes of this application the moisture content imparted into the substrate will be referred to generically as "lotion." Such lotions may be solutions, emulsions, or any other type of composition, and are typically some sort of aqueous cleansing formulation. A wide variety of such lotions is known in the art and is suitable.

Baby wet wipes are typically used by consumers for cleaning of the skin of infants and toddlers. Typical uses of baby wet wipes products include cleaning of the buttocks and perineal area during a diaper change, cleaning of the hands, face, and other body parts. The terms "baby wet wipes" and "wet baby wipes" are interchangeable and are meant to encompass wet wipe products which are specifically designed and targeted to be used by children ranging in age from newborn to toddlers and children in the 2-7 year old range. Such wipes for babies in the upper end of these age ranges are sometimes referred to as "toddler wipes" or "toddler toilet wipes" or by a similar designation. An example of such a product is the PAMPERS KANDOO wipe manufactured and sold by the Procter and Gamble Company of Cincinnati, Ohio. Even if sometimes commercially or informally referred to by a designation of other than "baby wipes" such products are expressly intended to be included within the definition of baby wet wipes as that term is used herein.

In one embodiment, a line-up of baby wet wipes may comprise two or more targeted or adapted individual baby wet wipe offerings. As used herein, the terms "targeted," "tailored," and "adapted to correspond" are meant to be interchangeable and are taken to mean that aspects of the products are specifically chosen to correspond to one or more aspects of a sub-segment of the baby wet wipes market as a whole. In particular, targeted or tailored elements are different among product offerings in the line-up on the basis of some aspect or attribute of the sub-population of baby wet wipes users to which the element is being targeted or adapted. For example, as illustrated in FIG. 3, individual baby wet wipes products in a line-up of such products may be targeted to two or more baby stages of development.

Referring to FIG. 3, the first line-up 310 includes disposable absorbent articles 312, 314, 316 and 318 suitable for a first, second, third and fourth stages of development, respectively. The second line-up 320 includes disposable wipes products 322, 324, and 326 suitable for a first, second and third/fourth stages of development, respectively. In one embodiment, first line-up 310 includes a common color scheme that is associated with the first line-up 310 of disposable absorbent articles and second line-up 320 includes a common color scheme that is associated with the second line-up 320 of disposable wipes products. In one example, the packages containing disposable absorbent articles 312, 314, 316 and 318 have a first line-up color 330, for example, purple, and the containers containing disposable wipes products 322, 324 and 326 have a second line-up color 340, for example, teal. As discussed previously, the use of a common color scheme across the first line-up facilitates consumers' understanding that the various disposable absorbent articles products are each part of a broader collective offering from the same company. Likewise, the use of a common color scheme across the second line-up facilitates consumers' understanding that disposable wipes products 322, 324 and 326 are each part of a broader collective offering from the same company.

The packaging for first line-up 310 and second line-up 320 also includes a stage color scheme that is associated with particular stages of development. For example, absorbent articles and wipes suitable for a first stage of development have a first stage color 350, for example, yellow, absorbent articles and wipes suitable for a second stage of development have a second stage color 352, for example, purple, absorbent articles suitable for a third stage of development and wipes suitable for a third/fourth stage of development have a third stage color 354, for example, red and absorbent articles suitable for a fourth stage of development have a fourth stage color 356, for example, blue or pink. As a result, the first stage color associated with the first line-up and the first stage color associated with the second line-up are substantially the same, while the second and third stage colors associated with the first line-up are substantially the same as the second and third stage colors associated with the second line-up. The use of a stage color scheme within each line-up that is associated with a particular stage of development is used to facilitate consumers' identification and selection of the appropriate absorbent article configuration/wipes product for a particular wearer/user.

Still referring to FIG. 3, in addition to providing a stage color scheme, the absorbent article configurations and wipes products may be displayed on store shelves in an arrangement that facilitates the consumer's selection. For example, the first, second, third and fourth absorbent article configurations of the first line-up, 312, 314, 316 and 318, respectively, may be arranged in a sequential order from the wearer's first stage of development to the wearer's fourth stage of development progressing from left to right across the first shelf 302. Similarly, the first, second and third disposable wipes products of the second line-up, 322, 324 and 326, respectively, may be arranged in a sequential order from the user's first stage of development to the user's third/fourth stage of development progressing from left to right across the second shelf 304.

As discussed above with respect to line-ups of disposable absorbent articles, packaging containing disposable wipes products may also include a stage communication system to communicate both brand benefits and the progressive nature of the wipes line-up more clearly to consumers. In one embodiment, the various offerings in the line-up may be expressly coordinated with each other though some sort of common indicia or indication. For example, a common set of icons representing the entire line-up and the position of a particular offering within the line-up could be employed. Such an icon system both communicates what the particular tailored product is adapted to correspond to (for example, a given stage of development) as well as what it is not corresponding to (for example, the other stages available). Both the positive and negative aspects of such a communication may assist purchasers in making choices of product better adapted to their product needs.

Line-ups of disposable absorbent articles and line-ups of disposable absorbent articles and disposable wipes products can also be provided with ancillary aides, tools, or selection mechanisms or devices to assist consumers in selecting the appropriate product in the line-up for their needs. For example, interactive displays including charts, wheels, kiosks, computer terminals, booklets, flyers or the like could describe attributes of stage of development and assist consumers in determining which stage their baby is in, and make a corresponding product recommendation within a particular line-up. Such guides could be offered on the package of a given product, otherwise on or near the shelf, or even removed from the point of purchase (such as on a web-site, telephone system, or through print media).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A merchandise display system for disposable absorbent articles, the system comprising:
   a first line-up of disposable absorbent articles,
      the first line-up including:
         an absorbent article of a first configuration corresponding to a child's first stage of development, the absorbent article of the first configuration being enclosed in a first package, wherein the first package includes a first line-up color corresponding to the first line-up and a first stage color corresponding to the first stage of development; and
         an absorbent article of a second configuration corresponding to a child's second stage of development, the absorbent article of the second configuration being enclosed in a second package, wherein the second package includes the first line-up color and a second stage color corresponding to the second stage of development; and
   a second line-up of disposable absorbent articles,
      the second line-up including:
         an absorbent article of a first configuration corresponding to a child's first stage of development, the absorbent article of the first configuration being enclosed in a first package, wherein the first package includes a second line-up color corresponding to the second line-up and a first stage color corresponding to the first stage of development; and
         an absorbent article of a second configuration corresponding to a child's second stage of development, the absorbent article of the second configuration being enclosed in a second package, wherein the second package includes the second line-up color and a second stage color corresponding to the second stage of development;
      wherein the first line-up color and the second line-up color are different; the first stage color associated with the first line-up and the first stage color associated with the second line-up are substantially the same; the second stage color associated with the first line-up and the second stage color associated with the second line-up are substantially the same; and the first line-up and the second line-up each contain indicia which communicates a common source or brand indicator to a consumer.

2. The merchandise display system of claim 1, wherein the first line-up further comprises an absorbent article of a third configuration corresponding to a child's third stage of development, the absorbent article of the third configuration being enclosed in a third package, wherein the third package includes a first line-up color corresponding to the first line-up and a third stage color corresponding to the third stage of development; and wherein the second line-up further comprises an absorbent article of a third configuration corresponding to a child's third stage of development, the absorbent article of the third configuration being enclosed in a third package, wherein the third package includes a second line-up color corresponding to the second line-up and a third stage color corresponding to the third stage of development; and wherein the third stage color associated with the first line-up and the third stage color associated with the second line-up are substantially the same.

3. The merchandise display system of claim 2, wherein the first line-up further comprises an absorbent article of a fourth configuration corresponding to a child's fourth stage of development, the absorbent article of the fourth configuration being enclosed in a fourth package, wherein the fourth package includes a first line-up color corresponding to the first line-up and a fourth stage color corresponding to the fourth stage of development; and wherein the second line-up further comprises an absorbent article of a fourth configuration corresponding to a child's fourth stage of development, the absorbent article of the fourth configuration being enclosed in a fourth package, wherein the fourth package includes a second line-up color corresponding to the second line-up and a fourth stage color corresponding to the fourth stage of development; and wherein the fourth stage color associated with the first line-up and the fourth stage color associated with the second line-up are substantially the same.

4. The merchandise display system of claim 3, wherein the fourth stage of development comprises a training stage.

5. The merchandise display system of claim 3, wherein the first, second, third and fourth absorbent article configurations of the first line-up are arranged in a sequential order from the child's first stage of development to the child's fourth stage of development.

6. The merchandise display system of claim 3, wherein the first, second, third and fourth absorbent article configurations of the second line-up are arranged in a sequential order from the child's first stage of development to the child's fourth stage of development.

7. The merchandise display system of claim 2, wherein the third stage of development comprises a learning stage.

8. The merchandise display system of claim 1, wherein the first stage of development comprises a bonding stage.

9. The merchandise display system of claim 1, wherein the second stage of development comprises an exploring stage.

10. The merchandise display system of claim 1, wherein the first line-up color is purple.

11. The merchandise display system of claim 1, wherein the second line-up color is teal.

12. The merchandise display system of claim 1, wherein the first line-up further comprises a stage communication system disposed on each of the first and second packages; the stage communication system comprising a brand indicator; a line-up indicator, the line-up indicator including visual indicia and narrative indicia; and a stage specific indicator; wherein the line-up indicator and stage specific indicator associate the first and the second absorbent article configurations with respective first and second stages of development, the association enabling a consumer to identify the appropriate absorbent article configuration for a wearer.

13. The merchandise display system of claim 1, wherein the brand indicator comprises a term corresponding to a brand of disposable absorbent article products.

14. A merchandise display system for baby care articles comprising:
 a first line-up of disposable absorbent articles, the line-up including:
  an absorbent article of a first configuration corresponding to a child's first stage of development, the absorbent article of the first configuration being enclosed in a first package, wherein the first package includes a first line-up color corresponding to the line-up of absorbent articles and a first stage color corresponding to the first stage of development; and
  an absorbent article of a second configuration corresponding to a child's second stage of development, the absorbent article of the second configuration being enclosed in a second package, wherein the second package includes the first line-up color and a second stage color corresponding to the second stage of development; and
 a second line-up of disposable wipes products, the line-up including:
  a first wipe product of a first configuration tailored to a child's first stage of development, the wipe product of the first configuration being enclosed in a first package, wherein the first package includes a second line-up color corresponding to the line-up of wipes products and a first stage color corresponding to the first stage of development; and
  a second wipe product of a second configuration tailored to a child's second stage of development, the wipe product of the second configuration being enclosed in a second package, wherein the second package includes the second line-up color and a second stage color corresponding to the second stage of development;
 wherein the first line-up color and the second line-up color are different; the first stage color associated with the first line-up and the first stage color associated with the second line-up are substantially the same; the second stage color associated with the first line-up and the second stage color associated with the second line-up are substantially the same; and the first line-up and the second line-up each contain indicia which communicates a common source or brand indicator to a consumer.

15. The merchandise display system of claim 14, wherein the first line-up color is purple.

16. The merchandise display system of claim 14, wherein the second line-up color is teal.

17. The merchandise display system of claim 14, wherein the first line-up further comprises an absorbent article of a third configuration corresponding to a child's third stage of development, the absorbent article of the third configuration being enclosed in a third package, wherein the third package includes a first line-up color corresponding to the first line-up and a third stage color corresponding to the third stage of development; and wherein the second line-up further comprises a disposable wipes product of a third configuration tailored to a child's third stage of development, the wipe product of the third configuration being enclosed in a third package, wherein the third package includes a second line-up color corresponding to the second line-up and a third stage color corresponding to the third stage of development; and wherein the third stage color associated with the first line-up and the third stage color associated with the second line-up are substantially the same.

18. The merchandise display system of claim 14, wherein the brand indicator comprises a term corresponding to a brand of baby care articles.

* * * * *